US006413720B1

(12) United States Patent
Pardinas et al.

(10) Patent No.: US 6,413,720 B1
(45) Date of Patent: Jul. 2, 2002

(54) METHOD FOR THE AFFINITY ISOLATION OF NEWLY SYNTHESIZED RNA

(75) Inventors: Jose R. Pardinas; Kyle W. H. Chan, both of San Diego, CA (US)

(73) Assignee: Signal Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/228,455

(22) Filed: Jan. 11, 1999

(51) Int. Cl.⁷ .......................... C12Q 1/68; C07H 21/02
(52) U.S. Cl. .......................... 435/6; 536/25.4; 536/23.1
(58) Field of Search ........................ 536/23.1, 25.4; 435/6

(56) References Cited

U.S. PATENT DOCUMENTS 5,888,727 A 3/1999 Lund et al. .................... 435/5

FOREIGN PATENT DOCUMENTS

| EP | 0 480 408 A1 | 4/1992 |
| WO | WO 97/07244 | 2/1997 |

OTHER PUBLICATIONS

Banfalvi et al. "Immunofluorescent visualization of DNA replication sites within nuclei of CHO cells" Hlstochemistry, vol. 93, No. 1, p. 81–86, 1989.*

Hiriyana et al. "Electron microscopic visualization of sites of nascent DNA synthesis by Streptavidin–gold binding to biotinylated nucleotides incorporated in vivo". J. Cell. Biol. Vol. 107, p. 33–44, 1988.*

Fenn and Herman, "Direct Quantitation of Biotin–Labeled Nucleotide Analogs in RNA Transcripts," *Analytical Biochemistry* 190:78–83, 1990.

Melvin et al., "Incorporation of 6–Thioguanosine and 4–Thiouridine into RNA," *Eur. J. Biochem.* 92:373–379, 1978.

Ono and Kawakami, "Separation of Newly–Synthesized RNA by Organomercurial Agarose Affinity Chromatography," *J. Biochem.* 81:1247–1252, 1977.

Roy et al., "Biotinylated RNA probes of the detection of potato spindle tuber viroid (PSTV) in plants," *Journal of Virological Methods* 23:149–155, 1989.

Woodford et al. "Selective Isolation of Newly Synthesized Mammalian mRNA after in Vivo labeling . . . " Analytical Biochemistry, 171, 1988, p. 166–172.*

Iborra et al. "Active RNA polymerases are localized within discrete transcription 'factories' in human nuclei" J. of Cell Science, 109, 1996, p. 1427–1436.*

McInnes et al. "Non–Racioactive Photobiotin–loabeled probes detect single copy genes and low abundance mRNA" Bio/Technology, vol. 5, 1987, p. 269–272.*

Brogi et al. "Indirect Angiogenic Cytokines Upregulate VEGF and bFGF Gene expression . . . " Circulation, vol. 90, No. 2, 1994, p. 649–652.*

Srivastava et al. "Purifying Nascent mRNA from Nuclear Run–On Assays . . . " BioFeedback, vol. 15, No. 2, 1993, p. 226–227.*

Dynal, Biomagnetic Techniques in Molecular Biology, 3rd Edition, 1998.*

Miller et al., "5'Mercuri UTP As A Substrate For Transcription," *Analytical Biochemistry* 123:94–100, 1982, Abstract Only.

Van De Walle et al., "Species of RNA Synthesized During Early Germination In The Radicle Of The Lentil Vicia–Lens Embryo," *Physiologia Plantarum* 57:181–188, 1983, Abstract Only.

\* cited by examiner

*Primary Examiner*—Jeffrey Fredman
*Assistant Examiner*—Jeanine Goldberg
(74) *Attorney, Agent, or Firm*—Pennie & Edmonds LLP

(57) ABSTRACT

Methods are provided for the isolation of newly synthesized mRNA. Such methods involve the incorporation of biotinylated rNTP analogues into cellular mRNA, and separating biotinylated mRNA from unlabeled RNA. The methods provided herein may be used, for example, for gene discovery, drug screens and studies of the regulation of gene expression.

14 Claims, 3 Drawing Sheets

METHOD FOR THE AFFINITY ISOLATION OF NEWLY SYNTHESIZED RNA

TECHNICAL FIELD

The present invention relates generally to the study of gene expression. The invention is more particularly related to methods for isolating newly synthesized RNA, and for using such RNA to evaluate the effect of various stimuli on gene expression.

BACKGROUND OF THE INVENTION

To understand a biological process at the molecular level, it is important to be able to identify genes that are differentially expressed in response to a stimulus. Some differentially expressed genes have been identified by isolating total mRNA before and after exposure to a stimulus, and identifying particular mRNAs that are present at different levels in the two mRNA pools. However, many such genes remain undetected because these pools of total mRNA contain mostly uninformative transcripts, due to the relatively long half-lives of most mRNAs (on the order of hours) within terminally differentiated eukaryotic cells.

Various differential and subtractive methods have been employed to facilitate the discovery of new differentially expressed genes. However, these techniques usually require considerable effort. In an attempt to facilitate the isolation of newly synthesized RNAs, phosphothioate analogues of nucleoside triphosphates have been employed (see, e.g., Melvin et al., *Eur. J. Biochem.* 92:373–379, 1978; Woodford et al., *Anal. Biochem.* 171:166–172, 1988; and Ono and Kawakami, *J. Biochem.* 81:1247–1252, 1977). Following incubation with such analogues, newly synthesized mRNAs can be isolated by organomercury affinity chromatography. Such techniques can permit the isolation of newly synthesized RNA, but the analogues can be toxic and can reduce the efficiency of transcription.

Accordingly, there is a need in the art for improved methods for preferentially isolating newly synthesized mRNAs, and for evaluating changes in gene expression as cells or tissues respond to stimuli. The present invention fulfills these needs and further provides other related advantages.

SUMMARY OF THE INVENTION

Briefly stated, the present invention provides methods for isolating populations of mRNAs that are enriched for newly synthesized transcripts, and for evaluating the effect of stimuli on cellular gene expression. Within one aspect, the present invention provides methods for isolating a population of mRNAs that is enriched for newly synthesized mRNA, comprising the steps of: (a) contacting a cell with a biotinylated rNTP analogue, such that the biotinylated rNTP analogue is incorporated into mRNA transcribed by the cell; (b) terminating transcription within the cell; and (c) separating biotinylated RNA from the cell, and therefrom isolating a population of mRNAs that is enriched for newly synthesized mRNA. Within certain embodiments, the biotinylated RNA may be separated from the cell by: (i) isolating RNA from the cell; (ii) contacting the RNA with streptavidin linked to a support material, such that biotinylated RNA binds to the streptavidin; and (iii) removing unbound RNA from the bound biotinylated RNA.

Within further aspects, the present invention provides methods for determining an effect of a stimulus on RNA transcription, comprising the steps of: (a) simultaneously or in either order, (i) contacting a cell with a biotinylated rNTP analogue, such that the biotinylated rNTP analogue is incorporated into mRNA transcribed by the cell; and (ii) exposing the cell to a stimulus; (b) terminating transcription within the cell; (c) determining a level of a biotinylated RNA in the cell; and (d) comparing the level in step (c) with a predetermined level for a similarly treated cell that is not exposed to the stimulus, and therefrom determining the effect of the stimulus on transcription of the RNA.

The present invention further provides, within other aspects, methods for identifying a gene that is differentially transcribed in cells exposed to a stimulus, comprising the steps of: (a) simultaneously or in either order, (i) contacting a cell with a biotinylated rNTP analogue, such that the biotinylated rNTP analogue is incorporated into mRNA transcribed by the cell; and (ii) exposing the cell to a stimulus; (b) terminating transcription within the cell; and (c) identifying a biotinylated RNA molecule that is present at a level that is altered relative to the level observed in similarly treated cells that are not exposed to the stimulus, and therefrom identifying a gene that is differentially transcribed in cells exposed to a stimulus.

Within other aspects, the present invention provides cDNA libraries prepared by a method comprising the step of reverse transcription of biotinylated mRNA prepared as described above; as well as isolated polypeptides produced by in vitro translation of a biotinylated mRNA molecule prepared as described above.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

Figure 1:
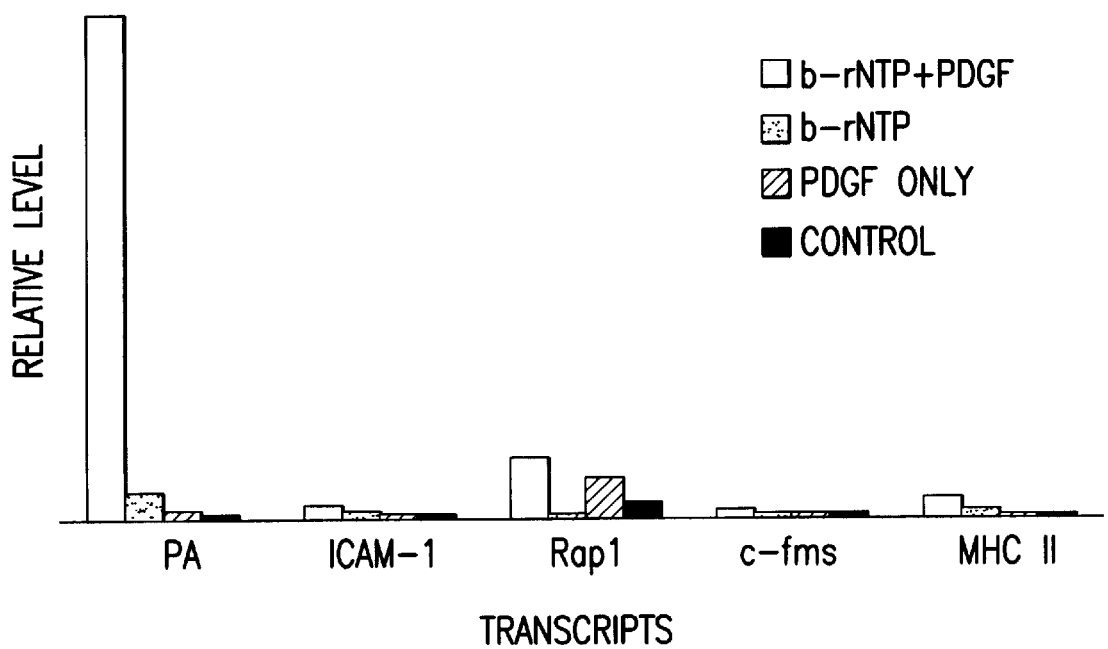
FIG. 1 is a histogram showing the relative levels of newly synthesized mRNA for the following genes: plasminogen activator (PA), intercellular adhesion molecule-1 (ICAM-1), ras-proximate-1 (Rap-1), M-CSF receptor (c-fms) and myosin heavy chain, isoform II (MHC II), as indicated. For each gene, cells were treated with and without biotin-rNTP and PDGF (as indicated), a cDNA library was prepared from each category of cells and the libraries were analyzed by PCR using specific primers.

As noted above, the present invention is generally directed to methods for isolating populations of mRNA that are enriched for newly synthesized transcripts and for evaluating stimulus-induced changes in cellular gene expression. The methods provided herein are based on the discovery that cells contacted with a biotinylated rNTP analogue rapidly incorporate the analogue into mRNA. The resulting biotinylated mRNA can be readily isolated by affinity techniques and used within a variety of methods, such as methods for evaluating alterations in gene expression.

As used herein, mRNA is "newly synthesized" if it is transcribed within a cell after exposure of the cell to a particular stimulus of interest. It will be apparent that newly synthesized mRNA may be transcribed over a relatively short period of time (e.g., 15–30 minutes) or over a longer period of time (on the order of hours) following exposure to the stimulus. A population of mRNA is considered to be "enriched" for newly synthesized mRNA if the population contains newly synthesized mRNA at a level that is statistically greater, preferably at least two fold greater and more preferably at least five fold greater, than the level within total mRNA isolated from cells similarly exposed to the stimulus. The extent of enrichment may be evaluated using any technique known in the art for quantitative measurement of transcript levels, including hybridization and PCR-based techniques.

In order to isolate newly synthesized mRNA, a cell is generally contacted with a biotinylated rNTP analogue under conditions and for a time sufficient to permit incorporation of the biotinylated rNTP analogue into mRNA transcribed within the cell. Any cell can be used within such analyses, provided that the biotinylated rNTP is taken up by the cell. Accordingly, any of a variety of cells may be employed, including cells in culture (e.g., human vascular smooth muscle cells) and in tissues, although for tissues that are removed from an animal, contact should take place within a relatively short time (generally within hours) to maximize incorporation of the rNTP analogue. Uptake of a biotinylated rNTP into a cell can be readily evaluated using a fluorescently labeled biotinylated rNTP. A fluorophor may be attached directly to the rNTP, along a linker, such as a long-chain carbon linker, or to the biotin, using techniques that are well known in the art. Cells of interest may then be exposed to a solution of fluorescent biotinylated rNTP in an amount and for a time sufficient to permit detectable incorporation (e.g. 500 $\mu$M for two hours). Cells may then be washed and harvested, and the level of incorporation assessed by any of a variety of well known methods such as, for example, semi-quantitative fluorescence microscopy or flow cytometry. Cells or tissues that exhibit fluorescence significantly above background (i.e., at least two fold greater than background) are suitable for the isolation of newly synthesized RNA as described herein.

Any biotinylated rNTP analogue may be used to label the newly synthesized transcripts, including biotinylated rCTP, rGTP, rTTP and rATP. Such analogues are generally commercially available (e.g., biotin-14-CTP is available from GIBCO, Grand Island N.Y.), or may be synthesized by techniques known in the art. The biotin may be attached directly to the rNTP, or may be attached via a linker. Any of a variety of well known linkers may be used. For example, certain suitable linkers contain a series of carbon atoms (e.g., 1 to 20). Other linkers of comparable length and flexibility may also be used.

Contact of the cell with the rNTP analogue is generally achieved by incubation in a medium appropriate for the particular cell. The duration of the incubation may vary depending on the goals of the analysis, but 30 minutes is generally sufficient for biotinylated rNTP present at 500 $\mu$M, and longer times may be useful in certain situations. It will be apparent that the incubation time and analogue concentration may be varied to optimize incorporation. For example, the analogue concentration may be any concentration that is not toxic to the cells, such as 1 $\mu$M to 10 mM, preferably 10 $\mu$M to 1 mM. Incubation time may be any time that results in significant incorporation of the analogue (e.g., a time sufficient to result in at least a three fold increase in fluorescence following incubation with a fluorescently labeled analogue as described above). Incubation times may vary between, for example, 15 minutes and many hours, with a typical incubation time ranging from 30 minutes to two hours.

Following contact with the rNTP analogue, transcription within the cell is terminated, e.g., by lysing the cell using any standard technique. Biotinylated mRNA may then be separated from the lysate. Within certain embodiments, such separation is performed by (1) isolating total RNA from the cell and (2) affinity purifying biotinylated mRNA from the total RNA. There are many techniques for isolating total RNA from a cell, and numerous kits are commercially available. The affinity purification is based on the ability of avidin to bind biotin. For example, total RNA may be contacted with a streptavidin column (e.g., AffiniTip™ streptavidin micro-column, GENOSYS, The Woodlands, Tex.), resulting in binding of biotinylated mRNA to the column. Unbound RNA may be removed by washing and purified biotinylated mRNA may then be released from the column using, for example, guanidinium hydrochloride or other compounds and techniques known in the art. If desired, the resulting mRNA may be further purified using standard techniques.

Within certain aspects, newly synthesized mRNA may be isolated before and after exposure of the cell to a stimulus, thereby permitting an evaluation of the effect of the stimulus on gene expression. Alternatively, the effect of two or more stimuli may be simultaneously evaluated. A stimulus may be any alteration in cellular environment, such as a chemical alteration (e.g., treatment with an agent of interest, such as a growth or differentiation factor or a pharmacological treatment), viral infection, a change in a culture parameter such as temperature or any other modification (e.g., a mechanical, viral or electrochemical stimulus or a modification in cell-cell adhesion). In general, to evaluate an early effect of the stimulus, cells are exposed to the stimulus and contacted with the biotinylated rNTP analogue simultaneously, or nearly simultaneously, although the order of these steps may vary. It will be apparent that, for an analysis of delayed changes in gene expression, cells may (but need not) be contacted with the rNTP analogue at intervals following exposure to the stimulus. Following termination of transcription, biotinylated mRNAs that are present at an altered level following the stimulus, relative to the level before the stimulus, may be identified using techniques such as hybridization and other methods known in the art and discussed herein. Alternatively, the effect of the stimulus on transcription of a particular gene may be evaluated by comparing the level of the particular mRNA in cells exposed to the stimulus with the level in cells not exposed to the stimulus.

When evaluating the effect of a stimulus, transcription may be terminated at multiple times following initiation of the stimulus. Suitable termination times may vary, but a typical range varies from 30 minutes to several hours after exposure to the stimulus. It will be apparent to those of ordinary skill in the art that longer or shorter exposure times may be appropriate depending on the particular stimulus.

Since long contact times with biotinylated rNTP may increase the background of housekeeping genes, such contact times are generally no longer than two hours. To evaluate delayed effects of a stimulus, contact with biotinylated rNTP is generally delayed. For example, to evaluate mRNA transcription at 25 hours after stimulation, contact with the biotinylated rNTP may be initiated, for example, 24 hours after stimulation. Alternatively, background may be reduced by limiting the amount of biotinylated rNTP (e.g., 5 μmol/kg body weight).

Within certain aspects of the present invention, biotinylated mRNA prepared as described above may be used directly for in vitro translation to generate proteins that can be analyzed using differential protein analyses (e.g., two-dimensional gel electrophoresis). Polypeptides generated by in vitro translation of biotinylated mRNA as described herein are specifically contemplated by the present invention.

Within other such aspects, the isolated biotinylated mRNAs may be assayed by hybridization with labeled cDNA probes. Such probes may be specific for a particular gene of interest, or multiple probes may be detected simultaneously. Such an assay is well suited to multiparametric DNA high throughput screens.

Within further aspects, the biotinylated mRNAs may be used for the preparation of a cDNA library. Such a library may be prepared using well known techniques that involve reverse transcription of the biotinylated mRNA molecules. Within certain embodiments, the mRNA may be amplified prior to preparation of the cDNA library. One suitable technique for amplifying the mRNA is known as long-accurate PCR (LA-PCR; see Taylor and Logan, *Curr. Opin. Biotechnol.* 6:24–29, 1995). Following reverse transcription, a cDNA library may be prepared using standard techniques and used within a variety of assays, such as those directed toward gene discovery. For example, a portion of the library may be restriction digested, normalized and cloned. The fragmented library may be screened using, for example, differential hybridization, random sequencing or quantitative virtual Northern analysis (i.e., a Northern blot analysis performed using cDNA instead of mRNA). Full-length genes of interest may be isolated from the undigested cloned library. The biotinylated mRNA or cDNA library may also be used as a starting material for other gene discovery techniques, such as cDNA library subtraction/normalization, DNA arrays and differential displays. By dramatically reducing the complexity of starting material, the success of such techniques may be significantly enhanced.

It should be noted that the methods described herein may be applied to eukaryotic and prokaryotic cells. Microbial gene expression is believed to be tightly regulated in response to environmental stress conditions. The ability of the microbes to respond to such stimuli by regulating gene expression is important for virulence (for review, see Foster et al., *Annu. Rev. Microbiol.* 49:145–174, 1995). One problem that has been encountered in the construction of cDNA libraries for the broad analysis of prokaryotic gene expression is the lack of 3' polyadenylation in the mRNA, which hampers the isolation of mRNA from total RNA. However, this difficulty can be circumvented using the methods provided herein. Following isolation of newly synthesized mRNA, specific adaptors may be attached to the mRNA ends (using standard methods) for further processing. This approach may further be applied to eukaryotic systems to identify subpopulations of nonpolyadenylated mRNAs.

Within a variety of methods provided herein, biotinylated mRNAs may be isolated at different time points and analyzed simultaneously using mRNA fingerprinting. This approach provides the transcription rate for multiple genes directly. In addition, the rate of transcript degradation for these genes may be obtained indirectly. This method may provide a quantitative analysis of mRNA turnover simultaneously for multiple genes.

The methods provided herein may also be used to map the effect of drugs and other agents on gene expression. The effect of different compounds may be readily compared by, for example, contacting cells with such compounds, isolating newly transcribed mRNA and performing a standard analysis such as RNA fingerprinting to evaluate gene expression.

Methods provided herein may also be applied to in vivo studies using laboratory animals such as mice. Biotin-rNTP may be administered by injection (e.g., in saline). A dose range for injection in an animal may be between 0.1 mg and 100 mg per kg body weight (or higher is no toxic effect is observed), preferably between 1 mg and 50 mg per kg body weight. Tissues may be harvested from an animal between 15 minutes and 2 hours after injection of biotin-rNTP (similar to times for in vitro cultures) either by sacrificing the animal or by surgical biopsy. Alternatively, blood may be collected to harvest mRNA from white blood cells for analysis. This analysis can be performed on animals treated with a stimulus such as a drug to identify effects on mRNA transcription. The differential effects between two or more stimuli or drugs on mRNA transcription in these animals may also be analyzed.

The following Examples are offered by way of illustration and not by way of limitation.

EXAMPLES

Example 1

Isolation of Newly Synthesized mRNA

This Example illustrates the isolation and characterization of a population of mRNA that is enriched for newly synthesized mRNA from human vascular smooth muscle cells.

A. Cell Culture

Human vascular smooth muscle cells (VSM) were grown in a 5% $CO_2$ atmosphere at 37° C. in Smooth Muscle Cell Growth Medium (Cell Applications, Inc., San Diego, Calif.). VSM were passaged by harvesting with 0.25% trypsin/EDTA, and were seeded at a 1:3 ratio ($3 \times 10^5$ cells/T75 or $1 \times 10^5$ cells/T25). Experimental cells at passages 10–15 were seeded onto gelatin-coated T25 flasks (2% gelatin for 1 hour at 37° C. followed by one rinse with PBS), and were grown to approximately 50% confluence. The cells were washed twice with PBS and incubated for two days in starvation medium [Medium 199 (Gibco, Grand Island, N.Y.) supplemented with 10 mM HEPES, 100 μg/ml gentamicin, 0.5% BSA, 0.2 mM $MgCl_2$, and 0.2 mM $MnCl_2$] prior to experimental treatment.

B. Labeling with Biotin-14-CTP

Starvation medium was removed, and 500 μM biotin-14-CTP (GIBCO, Grand Island, N.Y.) plus 10 ng PDGF-BB (Becton Dickinson, Franklin Lakes, N.J.) were simultaneously applied in 1 ml of starvation medium. Cells were harvested (trypsinized, pelleted in 1.5 ml Eppendorf tubes, and snap frozen in liquid nitrogen) after either 0.5, 1.0, or 2.0 hours of incubation. These cells are designated (+/+) biotin/PDGF. Control cells [(−/−) biotin/PDGF, (+/−) biotin/PDGF, and (−/+) biotin/PDGF] for each time point were similarly prepared.

C. RNA Isolation

Snap-frozen cell pellets were thawed on ice. Biotin-labeled cells were lysed with 500 µl of a 6M Urea/3M LiCl solution. The resulting lysate was homogenized by passing through a QIAshredder column (Qiagen, Valencia, Calif.). RNA was pelleted by centrifugation for 1 hour at 14,000 rpm and 4° C. The supernatant was decanted and the tubes were allowed to drain dry on clean paper towels. RNA from cells not labeled with biotin [i.e., (−/−) biotin/PDGF), and (−/+) biotin/PDGF controls] was isolated using TRIzol reagent (Gibco, Grand Island, N.Y.) according to a protocol supplied by the vendor.

RNA pellets from biotin-labeled cells were resuspended in 100 µl 1×Binding Buffer (5 mM Tris, pH 7.5, 1M NaCl, 0.5 mM EDTA, and 0.05% Tween 20). Biotinylated materials were captured using AffiniTip™ streptavidin microcolumns (Genosys, The Woodlands, Tex.) according to a protocol supplied by the vendor. Affinity-bound biotinylated RNA was released from the streptavidin columns with 100 µl 5M guanidinium hydrochloride. Eluted RNA was precipitated with 2.5 volumes of ethanol and 1 µl (20 µg/µl) glycogen (Boehringer Mannheim, Indianapolis, Ind.) followed by incubation at −20° C. for at least 1 hour. The RNA was pelleted by centrifugation at 14,000 rpm for 0.5 hour at 4° C., was washed with 75% ethanol, allowed to air dry and resuspended in 20 µl nuclease-free water.

D. Reverse Transcription and LA PCR Amplification

1 µg of each experimental and control RNA was reverse transcribed and PCR amplified using the SMART PCR cDNA Synthesis Kit (Clontech Laboratories, Palo Alto, Calif.) according to the SMART cDNA Synthesis for PCR-Select Subtraction protocol provided by the vendor. The linear amplification range was estimated, for each experimental and control cDNA population, using ethidium bromide stained gel visualization of PCR products at various number of cycles (as suggested by the vendor). The linear amplification range was also determined by blotting the aforementioned gels and probing successively with GAPDH, cyclophillin, and β-actin probes (i.e., Virtual Northern analysis). Mass amplification of each experimental and control cDNA population was carried out, in multiple identical reactions, using a number of PCR cycles already demonstrated to generate products well within the linear amplification range.

E. PCR Analysis of PDGF-BB Induced Genes 5 ng of double-stranded cDNA from each experimental and control cDNA population was used to PCR amplify a number of species that have been reported to be up-regulated by PDGF-BB in either rat or human vascular smooth muscle cells. Amplifications were carried out in a volume of 50 µl containing 0.1 µM each primer, 50 µM dNTP, 1×PCR buffer and 1 µl 50×Advantage cDNA Polymerase Mix (Clontech, Palo Alto, Calif.). Amplifications were carried out using a Perkin-Elmer thermocycler programmed for a 2 minute initial denaturation at 95° C., followed by 25–35 cycles of 95° C. for 30 seconds, 58° C. for 1 minute, and 72° C. for 1 minute, with a final 5 minute extension at 72° C. Products were analyzed on Ethidium bromide stained 1% agarose gel.

Figure 2:
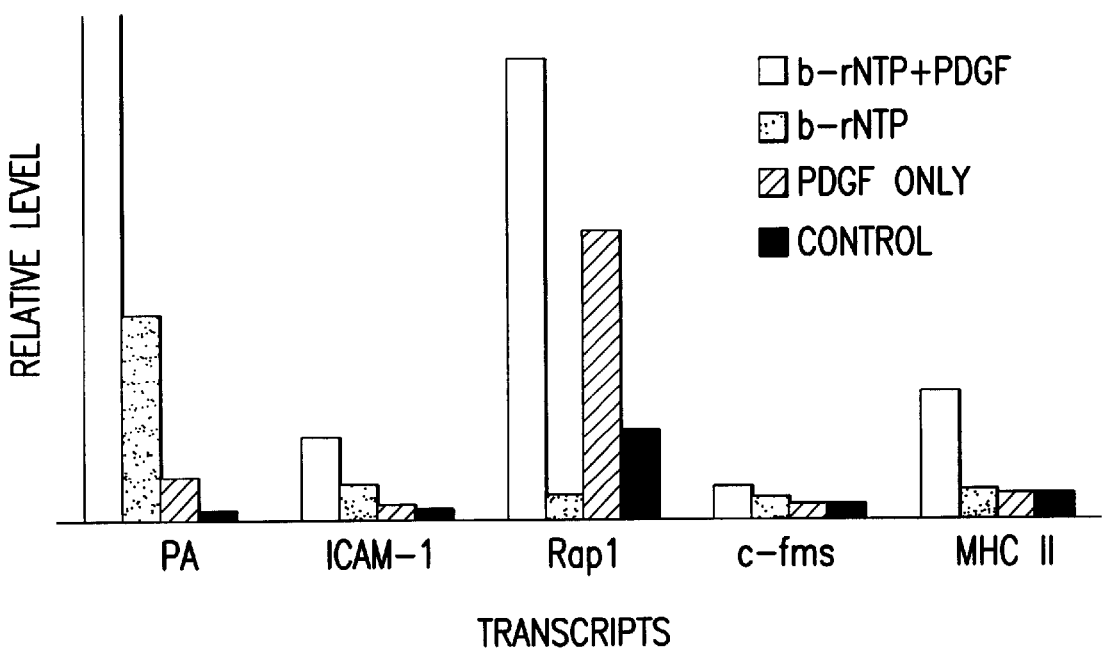
FIG. 2 is the same histogram shown in FIG. 1, with different Y axis scaling.

The results, which are presented in FIGS. 1 and 2, demonstrate the use of newly transcribed mRNA isolated as described herein for the analysis of differential gene expression.

F. RNA Fingerprinting

Up to 1 ng of double-stranded cDNA from each experimental and control population was used to carry out RNA fingerprinting analysis. For each reaction either one or two oligonucleotides of arbitrary sequence (and ranging in Tm from approximately 60° C. to 70° C.) were used. Reactions were carried out in a volume of 40 µl containing 5 nM each primer, 30 µM dNTP, 2 µCi [$^{33}$P]dATP (3000 Ci/mmol, Amersham), 1×ExTaq PCR reaction buffer, and 2 units of ExTaq DNA polymerase (PanVera Corporation, Madison, Wis.). Amplifications were carried out using a touch-down PCR strategy in a Perkin-Elmer thermocycler programmed for a 2 minute initial denaturation at 95° C., followed by two low-stringency cycles of 95° C. for 30 seconds, 50° C. for 2 minutes, and 72° C. for 2 minutes. These were followed by 25 high-stringency cycles of 95° C. for 30 seconds, 65° C. for 2 minutes, and 72° C. for 2 minutes. Newly transcribed mRNA was harvested by affinity chromatography.

Figure 3:
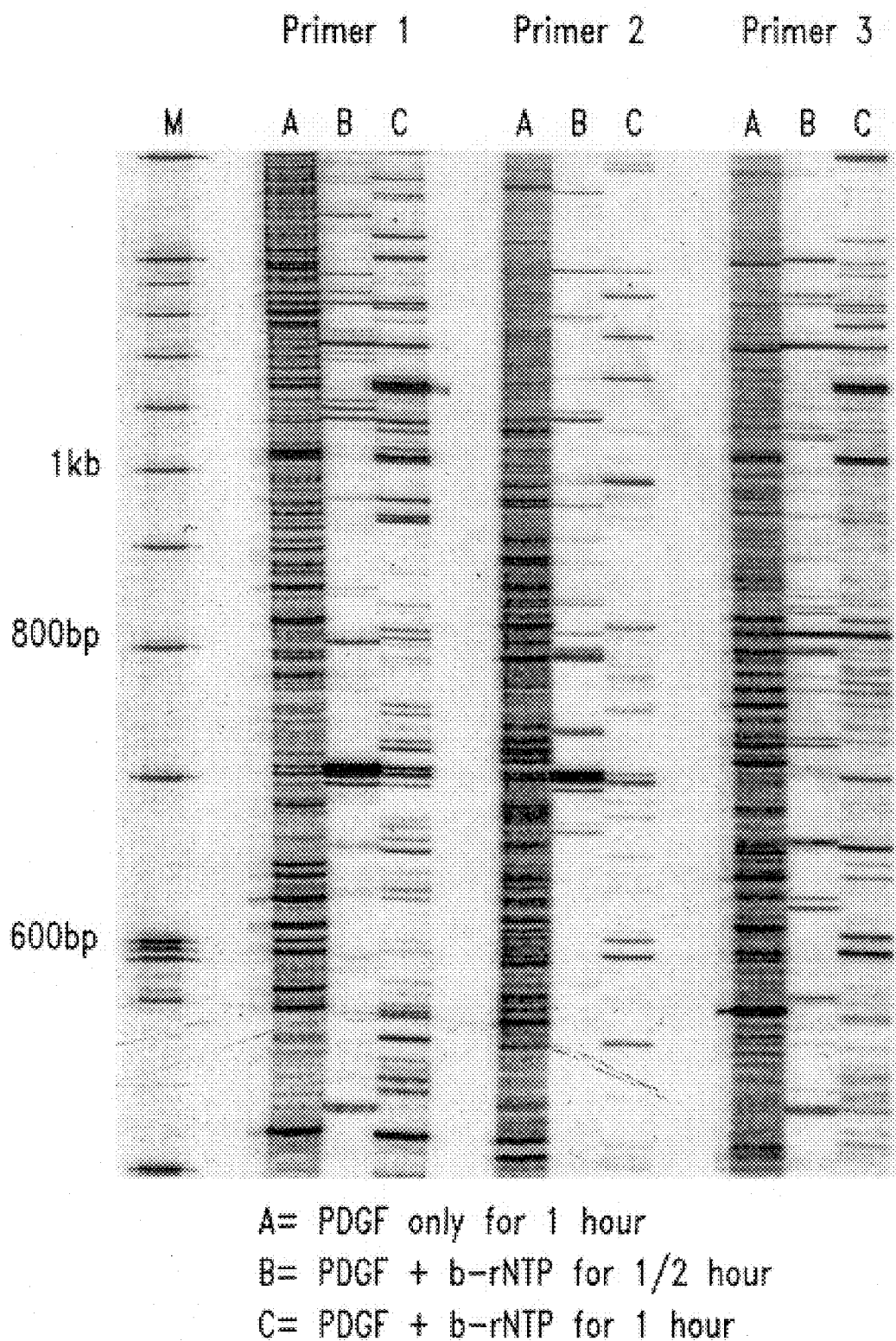
FIG. 3 is an autoradiogram illustrating RNA fingerprinting using biotinylated rNTP treated mRNA from vascular cells. Each lane labeled A shows the results after treatment with PDGF for 1 hour; each lane B shows the results for PDGF+ biotinylated rNTP for ½ hour and each lane C shows the results for PDGF+ biotinylated rNTP for 1 hour. Cells were treated as indicated and the newly transcribed mRNA was harvested by affinity chromatography. Primers 1, 2 and 3 were random primers.

The samples were denatured in formamide loading buffer and size-fractionated on denaturing 4% polyacrylamide gel. Gels were dried and autoradiographed. As shown in FIG. 3, the reduced complexity input of this technique allows for more rapid analysis of relevant genes within standard methods of differential gene analysis, such as differential display, RNA fingerprinting, cDNA library subtraction and normalization, differential hybridization, gene chip analysis and other methods.

Example 2

Diminished Toxicity of Biotinylated rNTP Analogues

This Example illustrates the minimal effect of biotinylated rNTP analogues on cell integrity.

Figure 4:
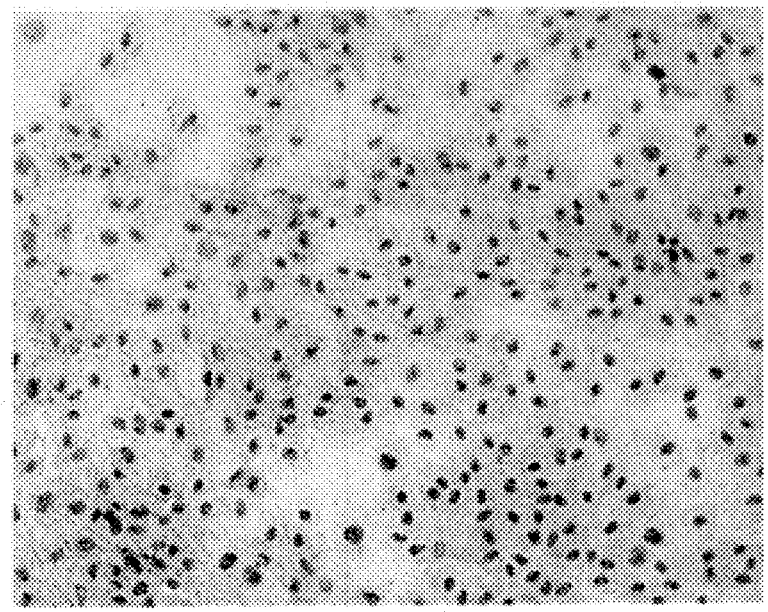
FIG. 4 is a micrograph of human immortalized vascular smooth muscle cells incubated with 6-thioguanosine (100 $\mu$M) for two hours, and then stained with Trypan blue.
Figure 5:
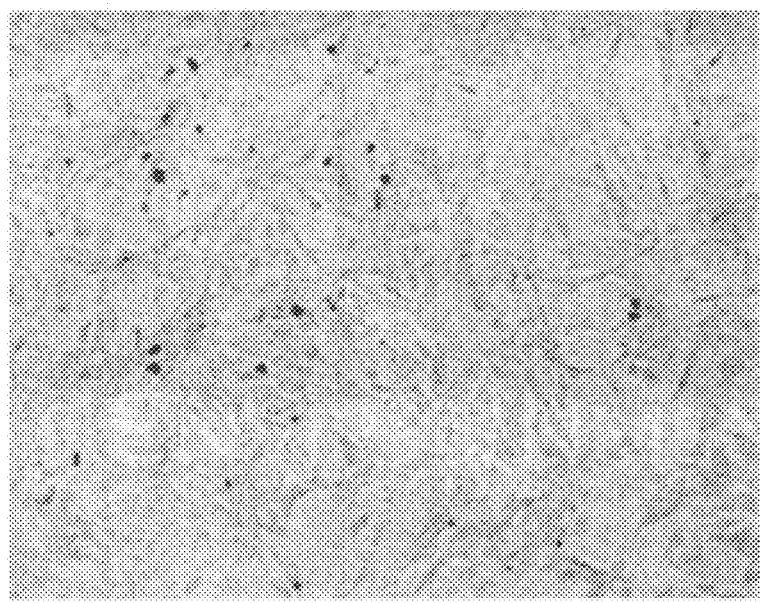
FIG. 5 is a micrograph of human immortalized vascular smooth muscle cells incubated with biotin-14-CTP (500 $\mu$M) for two hours, and then stained with Trypan blue.

Human immortalized vascular smooth muscle (VSM) cells were incubated with 6-thioguanosine (100 µM) or biotin-14-CTP (500 µM) for two hours, then stained with Trypan blue. Incorporation of the Trypan blue indicates that the integrity of the cell is compromised. Cells incubated with 6-thioguanosine took up the dye (FIG. 4), whereas very few cells incubated with the biotinylated analogue did. These results indicate that 6-thioguanosine is highly toxic and unsuitable as a neutral label for affinity purification of nascent mRNAs, and that biotin-rNTPs are superior for such purposes.

Example 3

Isolation of Newly Synthesized mRNAs in Bacteria

This Example illustrates the isolation of newly synthesized prokaryotic RNA suitable for expression studies.

Experimentally-induced bacterial RNAs were biotin-labeled in vivo, and affinity purified, essentially as described above for mammalian cells. Plasmid pBluescript II SK(+) (Stratagene, La Jolla, Calif.) was digested with Sma1, gel purified and dephosphorylated following a standard protocol (Sambrook et al. Molecular Cloning: A laboratory manual, 2$^{nd}$ ed., Cold Spring Harbor Laboratory Press, Cold Spring Harbor, N.Y., 1989). Complementary Deoxyoligonucleotide primers $Q_{T1}$ (5'-CCAGTGAGCAGAGTGACG AGGACTCGAGCTCAAGCTTTTTTTTTTTTTTTT-3') (SEQ ID NO:1) and $Q_{T2}$ (5'-AAAAAAAAAAAA AAAAAGCTTGAGCTCGAGTCCTCGTCACTCTGCT CACTGG-3') (SEQ ID NO:2) were annealed, and the resulting double-stranded oligonucleotide ($Q_{T3}$) was phosphorylated and cloned into predigested pBluescript II SK(+). Positive clones were identified by blue-white selection. Sequencing was used to check clone size, absence of mutations and orientation within the vector. In vitro transcription was carried out on linearized plasmid using T7 or T3 RNA polymerase following a standard protocol (Zhang and Frohman, Methods in Molecular Biology, Vol. 69:cDNA Library Protocols, Cowell and Austin, eds., Humana Press Inc., Totowa, N.J., 1997). The in vitro transcribed RNA oligo was ligated to the biotin-labeled affinity-purified bacterial RNAs using T4 RNA ligase according to a published protocol (Zhang and Frohman). Reverse transcription of the ligation products was carried, out using deoxyoligonucleotide primer $Q_0$ (5'-CCAGTGAGCAGAGTGACG-3') (SEQ ID NO:3) or $Q_1$ (5'-GAGGACTCGAGCTCAAGC-3') (SEQ ID NO:4) both of which are incorporated within $Q_{T3}$. The resulting single-stranded cDNA population was amplified using $Q_0$ or $Q_1$ and a commercially available LA PCR amplification kit and its accompanying protocol (Panvera Corporation, Madison, Wis.). The linear amplification range was determined by blotting 5 µl of the reaction over a number of cycles and probing with several standard housekeeping genes (e.g., GAPDH). Mass amplification of each experimental and control cDNA population was carried out, in multiple identical reactions, using a number of PCR cycles already demonstrated to generate products well within the linear amplification range. Mass-amplified materials were suitable reagents for a wide range of analytical techniques (e.g., RNA fingerprinting, cDNA library construction/screening, etc.).

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for isolating a population of mRNAs from cells in culture that is enriched for newly synthesized mRNA, comprising the steps of:
 (a) contacting a cell with a biotinylated rNTP analogue, wherein said contact has minimal effects on cell integrity as compared to cells in culture not contacted with the biotinylated rNTP analogue, such that the biotinylated rNTP analog is incorporated into mRNA transcribed by the cell, wherein said minimal effects on cell integrity are determined by an inability of said cell to incorporate Trypan blue;
 (b) terminating transcription within the cell; and
 (c) separating biotinylated RNA from the cell, and therefrom isolating a population of mRNAs that is enriched for newly synthesized mRNA.

2. A method according to claim 1, wherein the cell is contacted with a biotinylated rNTP analogue for an amount of time ranging from 30 minutes to two hours prior to termination of transcription.

3. A method according to claim 1, wherein transcription is terminated by lysing the cell.

4. A method according to claim 1, wherein the cell is a human vascular smooth muscle cell.

5. A method according to claim 1 wherein the biotinylated RNA is separated from the cell by:
 (a) isolating RNA from the cell;
 (b) contacting the RNA with streptavidin linked to a support material, such that biotinylated RNA binds to the streptavidin; and
 (c) removing unbound RNA from the bound biotinylated RNA.

6. A method according to claim 1, wherein the biotinylated rNTP analogue is biotin-14-CTP.

7. A method according to claim 1, wherein the biotinylated rNTP analogue is fluorescently labeled.

8. A method for isolating a population of mRNAs from cells in culture that is enriched for newly synthesized mRNA, consisting essentially of:
 (a) contacting a cell with a biotinylated rNTP analogue, such that the biotinylated rNTP analog is incorporated into mRNA transcribed by the cell, wherein integrity of cells is not compromised by incorporation of the rNTP analogues as compared to cells in culture not contacted with the biotinylated rNTP analogue;
 (b) terminating transcription within the cell; and
 (c) separating biotinylated RNA from the cell, and therefrom isolating a population of mRNAs that is enriched for newly synthesized mRNA.

9. A method according to claim 8, wherein the cell is contacted with a biotinylated rNTP analogue for an amount of time ranging from 30 minutes to two hours prior to termination of transcription.

10. A method according to claim 8, wherein transcription is terminated by lysing the cell.

11. A method according to claim 8, wherein the cell is a human vascular smooth muscle cell.

12. A method according to claim 8, wherein the biotinylated RNA is separated from the cell by:
 (a) isolating RNA from the cell;
 (b) contacting the RNA with streptavidin linked to a support material, such that biotinylated RNA binds to the streptavidin; and
 (c) removing unbound RNA from the bound biotinylated RNA.

13. A method according to claim 8, wherein the biotinylated rNTP analogue is biotin-14-CTP.

14. A method according to claim 8, wherein the biotinylated rNTP analogue is fluorescently labeled.

* * * * *

SEQUENCE LISTING

```
<160> NUMBER OF SEQ ID NOS: 4

<210> SEQ ID NO 1
<211> LENGTH: 52
<212> TYPE: DNA
<213> ORGANISM: Artificial Sequence
<220> FEATURE:
<223> OTHER INFORMATION: Description of Artificial Sequence:
      Deoxyoligonucleotide primer

<400> SEQUENCE: 1
ccagtgagca gagtgacgag gactcgagct caagcttttt ttttttttt tt          52

<210> SEQ ID NO 2
<211> LENGTH: 52
<212> TYPE: DNA
<213> ORGANISM: Artificial Sequence
<220> FEATURE:
<223> OTHER INFORMATION: Description of Artificial Sequence:
      Deoxyoligonucleotide primer

<400> SEQUENCE: 2
aaaaaaaaaa aaaaaaagct tgagctcgag tcctcgtcac tctgctcact gg          52

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:
      Deoxyoligonucleotide primers for reverse transcription

<400> SEQUENCE: 3
ccagtgagca gagtgacg                                                18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:
      Deoxyoligonucleotide primers for reverse transcription

<400> SEQUENCE: 4
gaggactcga gctcaagc                                                18
```